United States Patent [19]

Narula

[11] Patent Number: 4,882,777
[45] Date of Patent: Nov. 21, 1989

[54] CATHETER

[76] Inventor: Onkar S. Narula, 5765 S.W. 117th St., Miami, Fla. 33156

[21] Appl. No.: 40,517

[22] Filed: Apr. 17, 1987

[51] Int. Cl.$^4$ ............................................ A61M 25/00
[52] U.S. Cl. ................................................. 604/281
[58] Field of Search ................. 604/281, 280, 282, 21, 604/266, 264; 128/642, 786

[56] References Cited

U.S. PATENT DOCUMENTS

| | | | |
|---|---|---|---|
| 3,516,412 | 6/1970 | Ackerman | 128/786 |
| 4,117,836 | 10/1978 | Erikson | 604/281 |
| 4,135,518 | 1/1979 | Dutcher | 128/642 |
| 4,169,464 | 10/1979 | Obrez | 604/281 |
| 4,508,535 | 4/1985 | Joh et al. | 604/282 |
| 4,641,649 | 2/1987 | Walinsky et al. | 128/642 |

OTHER PUBLICATIONS

"Introducing: A New Decor ® Brachial—Coronary Anglographic Catheter", by Cordis Corporation, P.O. Box 428, Miami, Florida, 33137, 1973.
"A Decor ® Coronary Bypass Angiographic Catheter", by Cordis Corporation, P.O. Box 428, Miami Florida, 33137, 1974.

Primary Examiner—John D. Yasko
Attorney, Agent, or Firm—Fulwider, Patton, Lee & Utecht

[57] ABSTRACT

An improved catheter construction having a distal end and a proximal end, with a tip disposed at the distal end, the catheter having a complex "multi-planar" curvature to automatically position the distal end at a desired internal location within a biological subject, the catheter being formed of a resilient material having a memory, enabling deformation from and subsequent automatic return to the predetermined shape. Torque applied to the proximal end of the catheter, about the longitudinal axis of the catheter, passively affixes the distal end to the desired internal location.

11 Claims, 1 Drawing Sheet

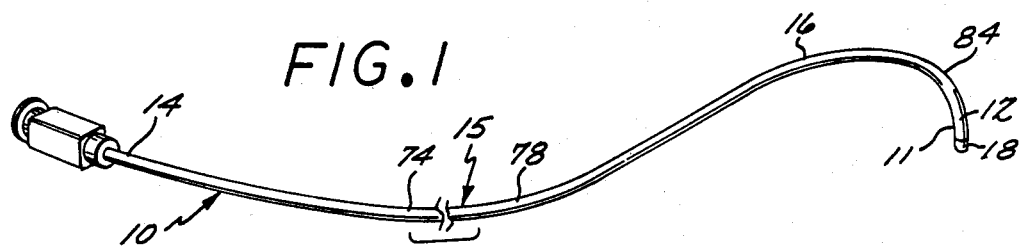
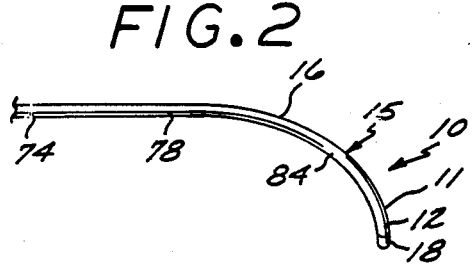
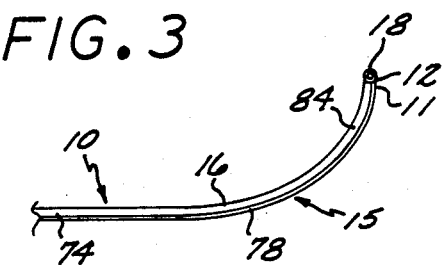
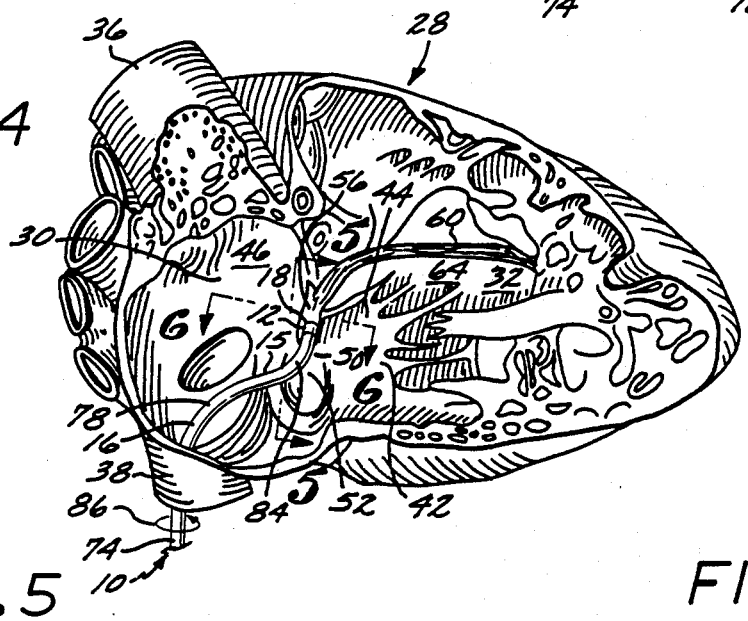
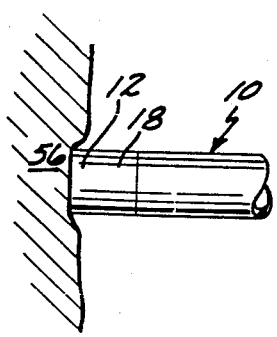
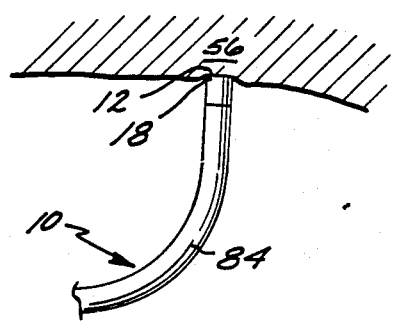

CATHETER

BACKGROUND OF THE INVENTION

This invention relates generally to medical apparatus and, more particularly, to a new and improved catheter tip design enabling very accurate and reliable intracardiac recording of and delivery of energy to the atrioventricular junction conductive tissue.

An electrode catheter technique has been developed to record electrical activation of the His bundle (atrioventricular or A-V bundle) and bundle branches via a pervenous femoral approach. With this technique an electrode catheter is inserted percutaneously via a femoral vein and advanced under fluoroscopic control through the inferior vena cava to the right atrium and across the tricuspid (right atrioventricular) valve into the right ventricle. The catheter tip is gradually withdrawn from the right ventricle into the right atrium and scraped along the interatrial septum until electrical activity of the His bundle is received. The His bundle activity is recorded as a rapid biphasic or triphasic potential sandwiched between atrial and ventricular activations. The tip of these prior art electrode catheters is either straight or gently curved in a single plane.

However, morphologically, the central longitudinal axis of the inferior vena cava is generally parallel to the interatrial septum. Since the bundle of His begins at the A-V node, laterally relative the inferior vena cava, the use of a straight or planar catheter tips prevents placing the tip in contact with the bundle of His. As a result, the catheter tip merely floats close to the desired location.

More specifically, since the catheter tip is not passively contacting the His bundle, it slides back and forth against the tricuspid valve, resulting in changes in the morphology and the amplitude of the detected electrical potential of the His bundle. It is believed that this is due to catheter tip motion, to and fro, across the valve and away from the septal leaflet. Because of this motion, the degree of separation between the endocardial surface of the His bundle and the recording electrode is never known and may vary from beat-to-beat or with respiratory movements. Variations in contact or the space between the electrode and the endocardium results in variations in the amplitude and morphology of the His bundle potential.

In addition, since the catheter tip is not fixed to the endocardial surface, a constant relationship between the electrode and the precise point on the A-V junction from which the electrical activity is being recorded is not maintained. As a result, the point upon the A-V junction from which electrical activity is being recorded may vary from beat-to-beat or with cardiac or respiratory motion.

During approximately the last five years, the His bundle recording technique has also been utilized for therapeutic purposes to ablate the His bundle by delivery of various types of energy, especially "DC shock" (the application of direct current voltage). This technique is described by J. Gallagher, et al. in "Catheter Technique For Closed-Chest Ablation Of The Atrioventricular Conduction System," *New England Journal of Medicine*, Vol. 306, No. 4, Jan. 28, 1982, pp. 194–200. This approach entails the recording of potentials by a standard His bundle recording technique, utilizing an electrode catheter and delivery of energy through the same catheter system. However, a moving and floating catheter tip does not maintain a good contact with the endocardial surface and thus the site at which the energy is being delivered. This may result in requiring a greater amount of energy to compensate for this method of delivery.

Hence, those concerned with the development and use of internal organ monitoring and electrostimulation systems in the medical field, e.g., intracardiac systems, have long recognized the need for improved catheters and electrode systems which enable a more accurate and reliable placement and contact of the catheter at the desired internal location. The present invention fulfills all of these needs.

SUMMARY OF THE INVENTION

Briefly, and in general terms, the present invention provides for maintaining greater precision in the positioning of the catheter's distal portion internally within an organism, which enables better, more reliable recordings from the desired location as well as improved electrical contact for delivery of energy to the desired site.

In a presently preferred embodiment, by way of example and not necessarily by way of limitation, the improved catheter of the present invention includes a specially shaped catheter tip for maintaining contact with a desired internal location, e.g., the endocardial surface adjacent the His bundle or atrioventricular (A-V) node.

More particularly, disposed at the distal portion of the catheter of the present invention is a tip which includes a complex curvature. This curvature automatically positions an electrode, disposed at the distal catheter end, at the desired internal location. The catheter is sufficiently resilient to deform to a generally linear configuration for insertion through a narrow tube, e.g. the subject's cardiovascular system, and return to the predetermined curvature upon exiting from such constraint.

In one preferred form, the catheter tip of the present invention includes a first or straight portion, to enter the heart via a femoral vein and inferior vena cava. Extending distally from this straight portion is a first curved portion to permit lateral catheter tip displacement relative the central longitudinal axis of the straight portion, e.g., from the left to the right when viewing the catheter from its proximal end. This structure permits the tip to traverse from the inferior vena cava across the tricuspid valve from the right atrium to the right ventricle.

A second curved portion extends distally from the first curved portion. The second curved portion imparts a three-dimensional aspect to the catheter of the present invention, by skewing the extreme distal end of the catheter relative to both the straight portion and the first curved portion. This structure permits rotation of the tip in the anteroposterior plane, allowing continuous contact with an interior surface that conventional catheters are unable to maintain, e.g., the endocardial surface at the A-V junction. Posterior rotation of the catheter tip about the catheter's central longitudinal axis and the continuous application of torque enables the tip to passively affix the catheter tip to the endocardial surface of the A-V node and the His bundle.

These and other objects and advantages of the invention will become apparent from the following more detailed description, when taken in conjunction with the accompanying drawings of illustrated embodiments.

DESCRIPTION OF THE DRAWINGS

FIG. 1 is a partial, perspective view of an improved catheter embodying features of the present invention;

FIG. 2 is a fragmentary, top view of an improved catheter in accordance with the present invention;

FIG. 3 is a fragmentary side elevational view of the improved catheter of the present invention;

FIG. 4 is a dorsal view of the interior of a human heart after removal of the sternocostal wall with the improved catheter of the present invention positioned therein, as for intracardiac recording;

FIG. 5 is an enlarged, fragmentary sectional view, taken substantially along the line 5—5 in FIG. 4; and FIG. 6 is an enlarged, fragmentary sectional view, taken substantially along the line 6—6 in FIG. 4.

DETAILED DESCRIPTION OF THE INVENTION

As shown in the exemplary drawings for the purposes of illustration, an improved catheter in accordance with this invention, referred to generally by the reference numeral 10, is provided for maintaining precise and continuous contact with a desired internal location.

More specifically as shown in FIG. 1, the catheter 10 of the present invention has a distal end 12 and a proximal end 14. A tip 15 disposed at a distal portion 11 of the catheter contains a complex curvature 16 so that the complex curvature will automatically position the distal end of the catheter at the desired internal location within a selected biological subject. An electrode or contact 18 is located at the distal end of the catheter. The specific complex curvature, not being limited to a single plane, and within the "memory" of the semi-flexible catheter, will automatically position the distal end adjacent the desired internal location and maintain reliable contact therewith. While one preferred embodiment is designed for use with intracardiac monitoring systems, or the delivery of electrical or thermal energy to the desired internal location, the present invention can be used for any internal monitoring or contact where precise and continuous contact is required.

Referring more specifically to FIG. 4, the mammalian heart 28 consists of four chambers including the right atrium 30 and right ventricle 32. The right atrium is in fluid communication with the superior vena cava 36 and the inferior vena cava 38. More particularly, the inferior vena cava opens into the most caudal part of the right atrium, facing cranialward and dorsalward. The atrioventricular junction, separates the right atrium from the right ventricle. The right atrioventricular or tricuspid valve 42, disposed within the junction, communicates the right atrium with the right ventricle. Three cusps or leaflets, one of which is the septal leaflet or cusp 44, form the tricuspid valve. The interatrial septum 46 separates the right atrium from the left atrium and is generally parallel to the longitudinal axis of the inferior vena cava.

The heart muscles are rhythmically stimulated by the heart contraction system. The pacemaker or initial nerve impulses are generated at the sinuatrial (S-A) node (not shown) and conducted to the atrioventricular (A-V) node 50. The A-V node lies near the orifice 52 of the coronary sinus in the interatrial septum 46. The bundle of His or atrioventicular (A-V) bundle 56 begins at the A-V node and follows along the membraneous interatrial septum towards the atrioventricular opening (not shown) and into membraneous interventricular septum a distance of one or two centimeters. At about the middle of the interventricular septum, the His bundle splits into the right (60) and left (not shown) branches, which stradle the summit of the muscular part of the interventricular septum 64. These bundle branches eventually connect to the terminal conducting fibers or Purkinje fibers. The Purkinje fibers effect the contraction of the other heart muscles upon activation by nerve impulses originating in the S-A node.

As a result of the spatial relationships of the above-described anatomical features, it should be recognized that the endocardial surface with which contact is desired, i.e., the portion adjacent the A-V node and His bundle, is generally lateral and parallel to the longitudinal axis of the inferior vena cava. This spatial relationship prevents conventional catheter tips, typically provided with a contact or electrode, from maintaining a continuous and perpendicular contact with the desired endocardial surface.

Referring now more specifically to FIGS. 1, 2 and 3, the catheter 10 of the present invention has a tip 15 disposed at a distal solution 11 adjacent the distal end 12 which is specially shaped to contain a complex curvature 16 so that the curvature will automatically position the distal end of the catheter or the tip and the electrode 18 positioned therein, at the desired precise internal location.

As best observed in FIG. 4, in one preferred form, the catheter of the present invention is used for inserting an electrode through a femoral vein (not shown) and the inferior vena cava 38 to contact an endocardial surface of a heart adjacent the ateroventricular (A-V) node 50 and the His bundle 56.

More specifically, as shown in FIGS. 1-4, the catheter 10 includes a specially shaped tip 15 disposed at a distal portion 11 of the catheter adjacent the distal end 12. The tip 15 comprises of a generally straight portion or segment 74 to permit movement generally along a central longitudinal axis, e.g., the patient's vascular system. This permits the extension of the distal end of the catheter within the interior of the subject being monitored, while retaining the proximal portion outside for connection to the desired recording, observing or electrostimulation device and for performing the desired rotation of the catheter tip to the desired degree. In one preferred form of the present invention, this straight longitudinal portion 74 is of sufficient length to extend from the site of initial pervenous entry to the desired internal location, e.g. to enter the heart via a femoral vein and the inferior vena cava by perveneous insertion.

In addition, the specially shaped tip 15 of the present invention includes a complexly curved portion 16 which provides a three-dimensional aspect and displaces the distal portion 11 of the catheter relative the straight portion 74. As shown more particularly in FIG. 4, in one preferred form for intracardiac recording and-/or applying electrical current, the catheter tip is designed for placing the electrode 18 adjacent the A-V node 50 and the His bundle 56. This includes a first curved portion 78, as best shown in FIG. 3, which curves in a generally arcuate manner to enable lateral displacement of the distal end 12 of the catheter 10 relative the straight portion. The first curved portion 78 of the improved catheter of the present invention enables the distal end 12 to extend laterally 30 relative the central longitudinal axis of the straight portion 74, a distance greater than the diameter of the blood vessel through which the catheter enters e.g., to traverse from the inferior vena cava across the tricuspid valve 42 into the right ventricle 32 from the right atrium 30. For purposes of illustration and not by way of limitation, the distal end 12 may be disposed laterally about one inch relative the central longitudinal axis of the straight portion 74. The straight portion 74 and the first curved portion 78, define a first plane generally parallel to the interatrial septum 46.

The first curved portion 78 terminates at a second curved portion 84 which is adjacent the distal end 12 of the catheter 10. At best shown in FIG. 2, this second curved portion 84, extending distally from the first portion 78, angles the distal end 12 outward relative the plane defined by the straight portion 74 and the first curved portion 78. In one preferred form, the tip 15 is substantially perpendicular to the plane defined by the straight portion and the first curved portion.

The particular angle and location which is particularly beneficial for locating the atrioventicular node and the His bundle may require a variation in the angles or particular location of the first and/or second curved portions. This allows the desired location of the distal end of the catheter with differently sized hearts. By way of example, the second curved portion 84 may be about one-quarter to about one-half inch from the distal end 12 of the catheter 10, and the first curved portion 78 about one to about two and one-half inches from the distal end.

The catheter 10 may be made of any material suitable for use in humans, e.g., any material having "memory" or permitting distortion from and subsequent substantial return to the desired three-dimensional or complex multi-planar shape. For the purposes of illustration and not limitation, the diameter of the catheter 10 may vary from about four to about eight "French" units (one "French" equals about one-third of a millimeter). The number of electrodes 18, as well as the inter-electrode distance and the shape of the electrodes, may be changed in any desired fashion to meet the various needs and goals of the specific task to be accomplished. However, once the appropriate shape of the catheter is determined, the shape is critical to the successful location, and maintenance of the catheter with the desired specific internal position, e.g., the A-V junction.

As shown more particularly in FIG. 4, the particular complexly curved portion and its connection to the straight portion, permits the rotation of the distal end 12 in an anteroposterior plane and left to right direction, about an arc having the central longitudinal axis of the straight portion 74 as its center. This rotation about the longitudinal axis of the straight portion, as indicated by the arrow 86 in FIG. 4, contacts the distal end of the catheter with the endocardial surface adjacent the A-V junction, e.g., the atrioventricular node and the His bundle. Maintaining a minimal amount of torque to the proximal end of the catheter provides the continuous contact and passive fixation of the catheter tip with the endocardial surface of the A-V node and the His bundle as shown in FIGS. 4–6.

In operation, an electrode catheter having the tip of the present invention is inserted percutaneously via a femoral vein and advanced under fluoroscopic control through the inferior vena cava 38 to the right atrium 30 and across the tricuspid valve 42 into the right ventricle 32. Because of the resilient nature of the catheter 10, the catheter may be distorted during this procedure to a generally longitudinal or straightlined shape as it travels through the cardiovascular system, until it reaches the desired internal location, e.g., the right atrium 30. Upon entry into the right atrium, the resilient nature and "memory" of the catheter enables the tip to revert to the desired complexly curved shape and orientation.

By this reversion to the desired predefined shape, the distal portion of the catheter, in conjunction with fluoroscopic viewing, will allow the direct and continuous contact of the distal end 12 of the catheter 10 with the specific internal surface desired. In addition, by providing sufficient torque to the proximal end 14, about the longitudinal axis of the straight portion 74 of the catheter, the electrode 18 or distal end 12 of the catheter can be maintained in the same position or surface portion of the endocardial structure. As a result, continuous and stable recordings of the proximal portion of the His bundle or A-V nodal-His bundle junction can be provided.

Upon entry of the catheter tip 15 into the right atrium 30, the tip is gradually withdrawn from the right ventricle 32 across the septal cusp 44 of the tricuspid valve 42 into contact with the interatrial septal wall 46 until electrical activity of the His bundle 56 is perceived. After locating the distal end 12 of the catheter at the desired internal position, the delivery of various types of chemicals or energy, for example, thermal, laser or direct current, may be applied to the His bundle to modify the electrical properties of the conduction system or ablate it for therapeutic purposes. Since the electrodes 18 or distal end 12 of the catheter and the endocardial surface to which electro-stimulation is to be applied is in good contact, there is no dilution of energy delivered due to the unfocused energy being dissipated over the entire cardiac chamber and lost in the circulating blood by a constantly moving catheter tip, as in conventional catheters. This has facilitated ablation of the His bundle with as little energy as about 4 to about 12 joules, as opposed to the 400 to 1800 joules typically necessary with previously available catheter techniques.

In one preferred form for use in thermal ablation techniques, it is desirable that the distal end of the catheter 10 include a heating element (not shown) in place of the electrode 14, to be oriented approximately perpendicular to the surface to be treated, in order to efficiently perform thermal ablation with the heating element. If the distal end 12 of the catheter 10 were to lay parallel or nearly parallel to the surface to be treated, good contact between the heating element and the area to be treated could not be insured. Accordingly, the distal portion of catheter 10 is preferably preformed into having the complex curvature 16 in order to insure generally perpendicular alignment between the distal end 12 and the surface to be treated. The shape is based on the relative orientations of the body vessel through which the catheter passes and the surface area to be treated. It will be understood that the shape of the catheter depends on the particular application and that shaping of the catheter is not necessary for all applications.

In the case where the catheter 10 is used for partial or complete thermal ablation of the A-V node 50 or His bundle 56 and the catheter is advanced into the heart through the fermoral vein, a double curvature is preferred. The preferred shape has the first gentle curved portion or bend 78 spaced by a first distance from the distal end 12 and the second gentle curved portion or bend 84 spaced by a second distance from the distal end 12. The distance to the first bend 78 is greater than the distance to the second bend 84. In this preferred embodiment, the distance between the first bend 78 and the distal end is about 3 cm, and the distance between second bend 84 and the distal end is about 1 cm. The first bend 78 is toward a first direction generally orthogonal to the longitudinal axis of the catheter and the second bend 84 is toward a second direction generally orthogonal to both the axis of the catheter and the first direction. Described another way, if the catheter 10 is oriented vertically, the first bend 78 is toward a left-to-right direction, and the second bend 84 is toward a front-to-rear direction. It will be understood that the distance between bends is variable depending on the size of the heart.

According to another feature of the improved catheter 10 of the present invention, the catheter 10 may be provided with a very gentle curve over a distance of about 10 cm to about 20 cm in a proximal direction from the first bend 78 in order to further assist in properly positioning the heating element relative to the A-V node and His bundle in the heart. The preferred shape can be imparted to the catheter 10 by heating the distal end 12 of flexible tube in a mold. The polymer material of the tube retains the "memory" of the shape after cooling.

As a result of the invention, the morphology and amplitude of the His bundle potential is maintained constant by the complex curvature 16 of the tip 15 and the torque applied at the proximal end 14. Hence, the electrode moves in unison with normal cardiac motion attendant to beating or respiratory motion, without losing contact with the recording or shock applying site. In addition, the improved catheter's ability to maintain contact with the endocardial surface adjacent the A-V node and His bundle, also permits the recording and delivery of energy to a precise focal point on the A-V junction rather than to the entire area of the A-V junction (1-2 centimeters). Due to the precise and continuing contact, the delivery of energy can be focused to an exact localized point.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A device for engaging a desired internal position within a biological subject lateral and oblique relative to the entry point, comprising:
  a catheter having a substantially straight portion, a distal end, a proximal end, a longitudinal axis extending from said distal end to said proximal end and a complex curvature extending longitudinally forward and laterally outward, said complex curvature extending from said distal end so that said curvature will automatically position said distal end of said catheter at said desired internal position.

2. A device as set forth in claim 1, wherein said complex curvature includes a first and second gently curved portions.

3. A device as set forth in claim 1, wherein said catheter is formed of a resilient material which has memory.

4. A device as set forth in claim 3, wherein said first gently curved portion is angled less than one-hundred and eighty degrees so that applying a minimal amount of torque to said proximal end urges said distal end into continuous contact and passive fixation at said desired position.

5. A catheter for inserting an electrode through a femoral vein and the inferior vena cava to contact an endocardial surface laterally outward from and parallel to the longitudinal axis of the interior vena cava of a heart, adjacent the atrioventricular node and the His bundle, comprising:
  an elongated resilient tubular member with a substantially straight portion terminating in a specially shaped tip, said tip including a first curved portion, a second curved portion, and a distal end, said first curved portion extending and gently bending laterally outward from said straight portion, said first curved portion and said straight portion defining a first plane and said second curved portion extending substantially perpendicular from said first plane and terminating in said distal end for maintaining said distal end in contact with said endocardial surface adjacent said atrioventricular node and said His bundle; and
  an electrode electrically connected through said elongated tubular member, said electrode positioned at said distal end.

6. A catheter as set forth in claim 5, wherein said first curved portion includes a single sweeping bend in a first direction extending laterally outward from said straight portion, and wherein said second curved portion is a second single bend in a second direction from said first curved portion.

7. A catheter as set forth in claim 5 wherein said first and second curved portions are gently curved less than one-hundred and eighty degrees to enable said tip to extend laterally a distance greater than the diameter of the femoral vein and inferior vena cava through which said catheter enters.

8. A catheter as set forth in claim 7, wherein said first curved portion is formed about one inch to about two and one-half inches from said distal end.

9. A catheter as set forth in claim 5, wherein said specially shaped tip has a complex, multi-planar curvature.

10. A catheter as set forth in claim 9, wherein said catheter is formed of a resilient material having memory.

11. A catheter as set forth in claim 8, wherein said second curved portion is about one-quarter to about one-half inch from said distal end.

* * * * *